United States Patent [19]

Wirth et al.

[11] Patent Number: 4,992,504
[45] Date of Patent: Feb. 12, 1991

[54] ETHER-CONTAINING OR THIOETHER-CONTAINING 1,3-DIKETONES AND THE USE THEREOF AS STABILIZERS FOR CHLORINE-CONTAINING POLYMERS

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 463,798

[22] Filed: Jan. 5, 1990

Related U.S. Application Data

[63] Continuation of Ser. No. 349,911, May 8, 1989, abandoned, which is a continuation of Ser. No. 239,232, Sep. 1, 1988, abandoned.

[30] Foreign Application Priority Data

Sep. 11, 1987 [CH] Switzerland .................. 3521/87

[51] Int. Cl.$^5$ .............. C08K 5/36; C08K 5/07; C07C 323/00; C07C 49/84; C07C 49/175
[52] U.S. Cl. .................. 524/357; 524/290; 524/317; 560/9; 560/55; 560/152; 560/179; 560/87; 568/42; 568/331; 568/336; 568/413
[58] Field of Search .................. 524/357, 317, 290; 568/42, 43, 331, 336, 337, 413; 560/9, 55, 152, 187, 179

[56] References Cited

U.S. PATENT DOCUMENTS

| | | | |
|---|---|---|---|
| 3,326,933 | 6/1967 | Wright | 548/378 |
| 4,102,839 | 7/1978 | Crochemore et al. | 524/354 |
| 4,221,687 | 9/1980 | Minagawa et al. | 524/357 |
| 4,371,651 | 2/1983 | Leistner et al. | 524/178 |

FOREIGN PATENT DOCUMENTS 3333987 10/1982 Fed. Rep. of Germany .

OTHER PUBLICATIONS

K. Hiroi et al., Chem. Pharm. Bull., 27, 2338 (1979).
K. Hiroi et al., Synthesis (1979), 621.
J. M. Hoffman et al., J. Med. Chem., 26, 1650 (1983).
O. Dann et al., Archic. Pharmazie, 292, 508 (1959).
J. Setsune et al., Chem. Express, 1, 216 (1986).

Primary Examiner—Veronica P. Hoke
Attorney, Agent, or Firm—Luther A. R. Hall

[57] ABSTRACT

Composition containing a chlorine-containing polymer and at least one compound of the formula IA

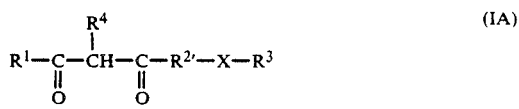

in which $R^1$ and $R^3$ independently of one another are $C_1$–$C_{12}$alkyl, phenyl, phenyl which is substituted by one to three $C_1$–$C_{12}$alkyl groups, $C_7$–$C_{10}$phenylalkyl or $C_7$–$C_{10}$phenylalkyl which is substituted on the phenyl ring by one to three $C_1$–$C_{12}$alkyl groups and $R^1$ is additionally —$R^2$—X—$R^3$, $R^{2'}$ is $C_1$–$C_{10}$alkylene, $R^4$ is hydrogen, $C_2$–$C_5$alkoxycarbonyl or $C_2$–$C_5$alkanoyl and X is oxygen or sulfur.

Compounds of the formula IA in which $R^{2'}$ is other than methylene are novel, with the exception of the compounds

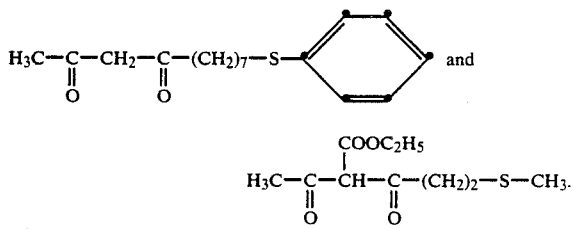

14 Claims, No Drawings

ETHER-CONTAINING OR THIOETHER-CONTAINING 1,3-DIKETONES AND THE USE THEREOF AS STABILIZERS FOR CHLORINE-CONTAINING POLYMERS

This is a continuation of application Ser. No. 349,911, filed on May 8, 1989, now abandoned, which in turn is a continuation of application Ser. No. 239,232, filed on Sept. 1, 1988, now abandoned.

The present invention relates to novel ether-containing or thioether-containing 1,3-diketones, to the use of 1,3-diketone derivatives for stabilizing a chlorine-containing polymer against the harmful effects of heat and/or light and to the chlorine-containing polymers which have been stabilized with these compounds.

It is known that chlorine-containing polymers have to be protected against the harmful effects of heat and/or light, particularly when they are processed to give mouldings. A heat stabilizer containing metal carboxylates and 1,3-diketones for polymers based on vinyl chloride is described in US-A 4,102,839. K. Hiroi et al. describe the preparation of 1-phenylthio-2,4-pentanedione in Chem. Pharm. Bull. 27, 2338-2344 (1979) and Synthesis 621-622 (1979). The use of mono-, di- or triketones containing 4-hydroxyphenylthio groups as colour developers for heat-sensitive recording material is described in German Offenlegungsschrift 3,333,987. US-A 3,326,933 discloses ether-containing 1,3-diketones and the use thereof as intermediates for the preparation of pharmaceuticals. J. M. Hoffman et al. describe the use of 1-benzyloxy-2,4-pentanedione as an intermediate in the preparation of a pyridine derivative in J. Med. Chem. 26, 1650-1653 (1983). The use of tetraketones containing sulfur or oxygen as stabilizers for polyvinyl chloride is known from US-A 4,371,651. O. Dann et al. describe the preparation of 3-ethoxycarbonyl-7-thiaoctane-2,4-dione in Archiv der Pharmazie 292, 508-518 (1959) and J. Setsune et al. describe the preparation of 1-phenylthio-8,10-undecanedione in Chem. Express 1, 216-219 (1986).

The present invention relates to compounds of the formula I

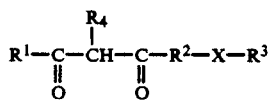

in which $R^1$ and $R^3$ independently of one another are $C_1$–$C_{12}$alkyl, phenyl, phenyl which is substituted by one to three $C_1$–$C_{12}$alkyl groups, $C_7$–$C_{10}$phenylalkyl or $C_7$–$C_{10}$phenylalkyl which is substituted on the phenyl ring by one to three $C_1$–$C_{12}$alkyl groups and $R^1$ is additionally $-R^2-X-R^3$, $R^2$ is $C_2$–$C_{10}$alkylene, $R^4$ is hydrogen, $C_2$–$C_5$alkoxycarbonyl or $C_2$–$C_5$alkanoyl and X is oxygen or sulfur, subject to the proviso that the compounds of the formula

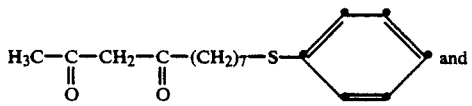 and

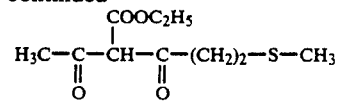

are excluded.

The compounds of the formula I have, for example, an advantageous effect on the colour stability of chlorine-containing polymers when the latter are processed by thermoplastic means. Their long-term stabilizing action is also noteworthy.

Examples of $R^1$ and $R^3$ as $C_1$–$C_{12}$alkyl are methyl, ethyl, propyl, butyl, tert-butyl, pentyl, hexyl, heptyl, octyl, 1,1,3,3-tetramethylbutyl, nonyl and decyl. $R^1$ is preferably $C_1$–$C_6$alkyl, especially methyl or tert-butyl. One of the preferred meanings of $R_3$ is $C_4$–$C_{12}$alkyl.

Examples of $R^1$ and $R^3$ as phenyl which can be substituted by one to three $C_1$–$C_{12}$alkyl, preferably $C_1$–$C_4$alkyl, groups are 2-methylphenyl, 2,5-dimethylphenyl, 2,4,6-trimethylphenyl or 2-, 3- or 4-n-dodecylphenyl.

Examples of $R^1$ and $R^3$ as $C_7$–$C_{10}$phenylalkyl which can be unsubstituted or substituted on the phenyl ring by one to three $C_1$–$C_{12}$alkyl groups are benzyl, α-methylbenzyl, 2-methylbenzyl, 2,5-dimethylbenzyl, 2,4,6-trimethylbenzyl and 2-, 3- or 4-n-dodecylbenzyl. Benzyl and benzyl which is substituted on the phenyl ring by n-dodecyl are preferred.

Examples of $R^2$ as $C_2$–$C_{10}$alkylene which can be linear or branched are ethylene, trimethylene, 2-methylethylene, tetramethylene, 3-methyltrimethylene, pentamethylene, hexamethylene, octamethylene and decamethylene. $R_2$ is preferably $C_2$–$C_4$alkylene, in particular $C_3$–$C_4$alkylene. $R_2$ is particularly preferably trimethylene.

Examples of $R^4$ as $C_2$–$C_5$alkoxycarbonyl are methoxycarbonyl, ethoxycarbonyl, propoxycarbonyl or butoxycarbonyl, preferably tert-butoxycarbonyl.

Examples of $R^4$ as $C_2$–$C_5$alkanoyl are acetyl, propanoyl, butanoyl or pentanoyl. Acetyl is preferred.

Compounds of interest are those of the formula I, subject to the proviso that compounds of the formula

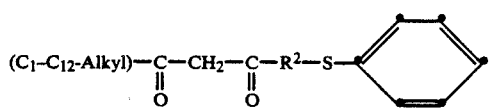

in which $R^2$ is as defined above are excluded.

X is preferably sulfur.

Compounds of particular interest are those of the formula I in which $R^1$ and $R^3$ independently of one another are $C_1$–$C_{12}$alkyl, phenyl, phenyl which is substituted by one to three $C_1$–$C_{12}$alkyl groups, benzyl or benzyl which is substituted on the phenyl ring by one to three $C_1$–$C_{12}$alkyl groups.

Compounds of the formula I in which $R^4$ is hydrogen are preferred.

Compounds of the formula I in which $R^4$ is $C_2$–$C_5$alkoxycarbonyl or $C_2$–$C_5$alkanoyl are also preferred.

Compounds of the formula I in which $R^1$ is $C_1$–$C_{12}$alkyl, phenyl, phenyl which is substituted by one to three $C_1$–$C_4$alkyl groups, benzyl or benzyl which is substituted on the phenyl ring by one to three $C_1$–$C_4$alkyl groups are likewise preferred.

In accordance with a further preference, $R^1$ is $C_1$–$C_6$alkyl, phenyl or phenyl which is substituted by one to three methyl groups and $R^3$ is $C_4$-$C_{12}$alkyl, phenyl, benzyl or benzyl which is substituted on the phenyl ring by n-dodecyl.

Compounds of the formula I which are additionally preferred are those in which $R^1$ is $C_1$-$C_4$alkyl or phenyl, $R^2$ is $C_2$-$C_4$alkylene and $R^3$ is $C_4$-$C_{12}$alkyl, phenyl or benzyl.

Compounds of the formula I which are particularly preferred are 1-benzyl-thio-3,5-hexanedione, 1-phenylthio-4,6-heptanedione, 1-(n-dodecylthio)-4,6-heptanedione and 1-phenoxy-4,6-heptanedione.

The invention also relates to compositions containing a chlorine-containing polymer and at least one compound of the formula IA $$R^1-\underset{\underset{O}{\|}}{C}-\underset{\underset{}{R^4}}{CH}-\underset{\underset{O}{\|}}{C}-R^{2'}-X-R^3 \quad (IA)$$

in which $R^1$ and $R^3$ independently of one another are $C_1$-$C_{12}$alkyl, phenyl, phenyl which is substituted by one to three $C_1$-$C_{12}$alkyl groups, $C_7$-$C_{10}$phenylalkyl or $C_7$-$C_{10}$phenylalkyl which is substituted on the phenyl ring by one to three $C_1$-$C_{12}$alkyl groups and $R^1$ is additionally $-R^{2'}-X-R^3$ $R^{2'}$ is $C_1$-$C_{10}$alkylene, $R^4$ is hydrogen, $C_2$-$C_5$alkoxycarbonyl or $C_2$-$C_5$alkanoyl and X is oxygen or sulfur.

$R^{2'}$ is preferably $C_2$-$C_{10}$alkylene.

Compositions which are of interest are those containing a chlorine-containing polymer and at least one compound of the formula IA in which the variables $R^1$, $R^{2'}$, $R^3$, $R^4$ and X have the preferred meanings indicated above under the formula I, the variable $R^{2'}$ corresponding to the radical $R^2$.

The following are examples of compounds of the formula IA:

(a) $H_3C-CO-CH_2-CO-CH_2CH_2-S-CH_2-\text{Ph}$ (b) $H_3C-CO-CH_2-CO-CH_2CH_2-S-C_4H_9\text{-n}$ (c) $H_3C-CO-CH_2-CO-CH_2-S-C_4H_9\text{-t}$ (d) $H_3C-CO-CH_2-CO-CH_2-S-C_8H_{17}\text{-t}^{(1)}$ (e) $H_3C-CO-CH_2-CO-CH_2CH_2-S-C_{12}H_{25}\text{-n}$ (f) $H_3C-CO-CH_2-CO-CH_2CH_2-S-C_{12}H_{25}\text{-t}$ (g) $H_3C-CO-CH_2-CO-CH_2-S-CH_2-\text{Ph}$ (h) $H_3C-CO-CH_2-CO-CH_2CH_2CH_2-S-C_{12}H_{25}\text{-n}$ (i) $t\text{-}H_9C_4-CO-CH_2-CO-CH_2CH_2-S-CH_2-\text{Ph}$ (j) $t\text{-}H_9C_4-CO-CH_2-CO-CH_2CH_2-S-C_{12}H_{25}\text{-n}$ (k) $t\text{-}H_9C_4-CO-CH_2-CO-CH_2CH_2-S-C_8H_{17}\text{-n}$ (l) $t\text{-}H_9C_4-CO-CH_2-CO-CH_2-S-CH_2-\text{Ph}$ (m) $t\text{-}H_9C_4-CO-CH_2-CO-CH_2-S-C_8H_{17}\text{-t}$ (n) $t\text{-}H_9C_4-CO-CH_2-CO-CH_2CH_2CH_2-S-CH_2-\text{Ph}$ (o) $t\text{-}H_9C_4-CO-CH_2-CO-CH_2CH_2CH(CH_3)-S-CH_2-\text{Ph}$ (p) $t\text{-}H_9C_4-CO-CH_2-CO-CH_2CH_2CH(CH_3)-S-C_8H_{17}\text{-n}$ (q) $t\text{-}H_9C_4-CO-CH_2-CO-CH_2-S-C_6H_{13}\text{-n}$ (r) $\text{Ph}-CO-CH_2-CO-CH_2CH_2-S-CH_2-\text{Ph}$ (s) $\text{Ph}-CO-CH_2-CO-CH_2-S-C_{12}H_{25}\text{-t}$ (t) $\text{Ph}-CO-CH_2-CO-CH_2CH_2CH_2-S-CH_2-\text{Ph}$ (u) $\text{Ph}-CO-CH_2-CO-CH_2CH_2CH(CH_3)-S-CH_2-\text{Ph}$ (v) $\text{Ph}-CO-CH_2-CO-CH_2CH_2CH_2-S-C_{12}H_{25}\text{-n}$ (w) $\text{Ph}-CO-CH_2-CO-CH_2CH_2CH(CH_3)-S-C_{12}H_{25}\text{-}t^{(2)}$ (x) $\text{Ph}-CO-CH_2-CO-CH_2-S-C_6H_{13}\text{-n}$ (y) $3\text{-}CH_3\text{-}C_6H_4-CO-CH_2-CO-CH_2CH_2-S-CH_2-\text{Ph}$ (z) $2\text{-}CH_3\text{-}C_6H_4-CO-CH_2-CO-CH_2CH_2-S-C_{12}H_{25}\text{-n}$ (A) $2,4,6\text{-}(CH_3)_3\text{-}C_6H_2-CO-CH_2-CO-CH_2-S-C_{12}H_{25}\text{-t}$ (B) $2\text{-}CH_3\text{-}C_6H_4-CO-CH_2-CO-CH_2-S-CH_2-C_6H_4\text{-}C_{12}H_{25}$ (C) $H_3C-CO-CH_2-CO-CH_2CH_2-S-CH_2-C_6H_4\text{-}C_{12}H_{25}$

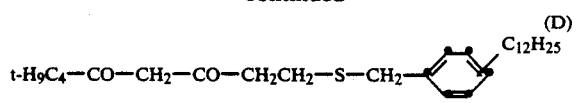 (D)

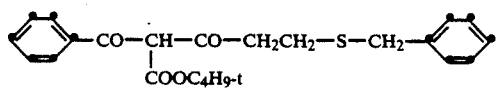 (E)

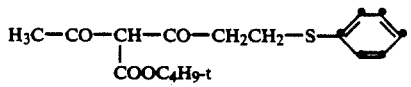 (F)

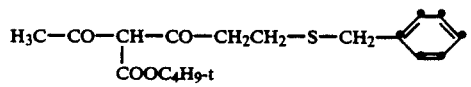 (G)

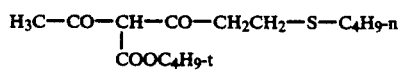 (H)

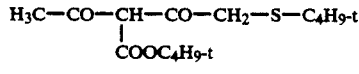 (I)

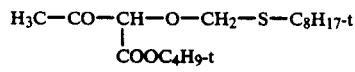 (J)

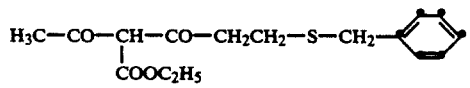 (K)

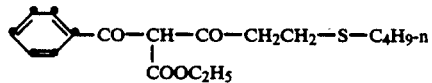 (L)

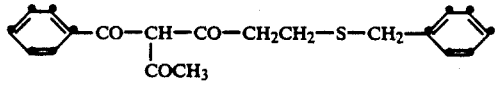 (M)

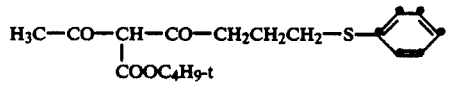 (N)

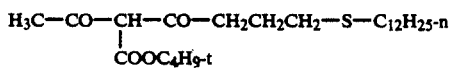 (O)

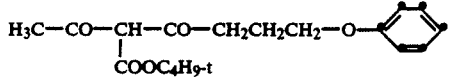 (P)

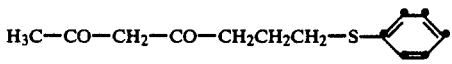 (Q)

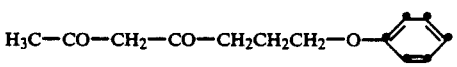 (R)

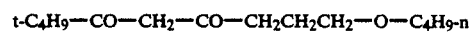 (S)

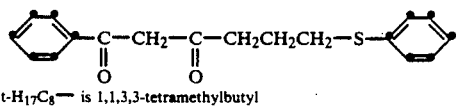 (T)

[1] t-$H_{17}C_8$— is 1,1,3,3-tetramethylbutyl
[2] t-$H_{25}C_{12}$— is, for example, a radical such as is described for tertiary dodecylmercaptan in "Ullmanns Enzyklopadie der technischen Chemie ("Ullmann's Encyclopaedia of Industrial Chemistry"), 4th edition, Volume 23, pages 181 and 182, Verlag Chemie, Weinheim".

The compounds (a), (b), (h), (r), (v), (G), (K), (L), (M), (N), (O), (P), (Q), (R), (S) and (T) are of interest. The compounds (a), (h), (v), (O), (P), (Q), (R), (S) and (T), in particular the compounds (a), (h), (Q) and (R), are preferred.

The chlorine-containing polymers are preferably vinyl chloride homopolymers or copolymers. The following are examples of suitable comonomers for the copolymers: vinyl acetate, vinylidene chloride, trans-dichloroethylene, ethylene, propylene, butylene, maleic acid, acrylic acid, fumaric acid and itaconic acid Other suitable chlorine-containing polymers are post-chlorinated PVC and chlorinated polyolefins, and also graft polymers of PVC with EVA, ABS and MBS. Also preferred as substrates are mixtures of the abovementioned homopolymers and copolymers, in particular vinyl chloride homopolymers, with other thermoplastic and/ or elastomeric polymers, in particular with ABS, MBS, NBR, SAN and EVA.

Suspension and bulk polymers as well as emulsion polymers are also preferred.

Polyvinyl chloride and copolymers of vinyl chloride are particularly preferred as the chlorine-containing polymer.

It is advantageous to employ the compounds of the formula IA together with known heat stabilizers, for example Me(II) phenates, in particular $C_7$-$C_{20}$alkylphenates, for example nonylphenate, or Me(II) carboxylates. Me(II) is, for example, Ba, Ca, Mg, Cd or Zn. The carboxylates are preferably salts of carboxylic acids having 7 to 20 C atoms, for example benzoates, alkenoates or alkanoates, preferably stearates, oleates, laurates, palmitates, hydroxystearates or 2-ethylhexanoates. Stearates, oleates and p-tert-butylbenzoates are particularly preferred.

In addition, the chlorine-containing polymers can contain customary quantities of conventional PVC stabilizers, for example epoxy compounds, such as epoxidized oils and, preferably, epoxidized fatty acid esters, in particular epoxidized soya bean oil, and also phosphites, preferably those of the formulae

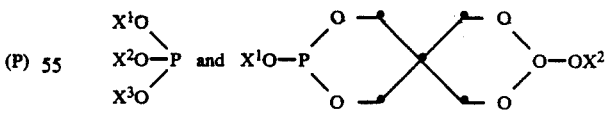

in which $X^1$, $X^2$ and $X^3$ independently of one another are $C_4$-$C_{18}$alkyl, phenyl or phenyl which is substituted by one to three $C_1$-$C_{12}$alkyl groups.

Organic phosphites which are particularly preferred are distearylpentaerythrityl diphosphite, trisnonylphenyl phosphite and phenyldidecyl phosphite.

The known heat stabilizers (for example carboxylates) can be present in the material to be stabilized in a concentration known to those skilled in the art, for example in amounts of 0.05 to 5% by weight.

The phosphites are employed, for example, in concentrations of 0.3 to 5, preferably 0.5 to 1, % by weight, and the epoxy compounds, for example the epoxidized soya bean oil, are employed in concentrations of 2 to 8, preferably 1 to 3, % by weight.

The compounds of the formula IA are incorporated into the chlorine-containing polymer, for example, in amounts of 0.05 to 1, preferably 0.1 to 0.5, % by weight.

The term % by weight relates in each case to the material to be stabilized.

Chlorine-containing polymers containing at least one compound of the formula IA and, in addition, an epoxy compound and at least one Me(II) carboxylate and/or Me(II) phenate and, if appropriate, a phosphite are preferred; Me(II) is Ca, Ba, Mg, Cd or Zn.

In accordance with a further preference the chlorine-containing polymers according to the invention contain at least one compound of the formula IA, epoxidized soya bean oil and at least one Me(II) carboxylate, Me(II) being Ca, Ba, Mg or Zn, especially Zn. Mixtures of Ba/Zn carboxylates or Ca/Zn carboxylates are particularly preferred as co-stabilizers in this case.

Depending on the end use of the polymers, it is also possible to incorporate further additives, for example phenolic antioxidants, lubricants (preferably montan waxes or glycerol esters), fatty acid esters, paraffins, plasticizers, fillers, carbon black, asbestos, kaolin, talc, glass fibres, modifiers (for instance high-impact additives), fluorescent brighteners, pigments, light stabilizers, UV absorbers, fire-retarding agents or antistatic agents, before or during the incorporation of the stabilizers.

The incorporation of the stabilizer components into the chlorine-containing polymer is effected most advantageously, in the customary manner, on a 2-roll mill at temperatures between 150° and 200° C. In general, an adequate homogenization can be obtained within 5 to 15 minutes. The addition of the components can be carried out individually or together, in the form of a premix. A liquid premix has proved advantageous, i.e. the process is carried out in the presence of inert solvents and/or plasticizers.

The compounds of the formula IA in which $R^4$ is hydrogen can be prepared analogously to known processes, for example by reacting a compound of the formula II

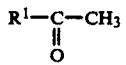

(II)

in which $R^1$ is as defined above with a compound of the formula III

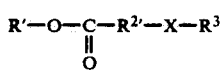

(III)

in which X, $R^{2'}$ and $R^3$ are as defined above and R' is preferably $C_1$-$C_3$alkyl, in the presence of a strongly basic compound, for example an alkali metal alcoholate, hydride or amide or a magnesium alcoholate, hydride or amide, in particular sodium methylate or sodium ethylate. The reaction is preferably carried out in an inert solvent, for example toluene, xylene or tetrahydrofuran. The reaction temperature is advantageously "20° C. up to the boiling point of the solvent selected". The primary reaction product is the alkali metal chelate or magnesium chelate of the corresponding diketo derivative, which can be split by acids, for example hydrochloric acid, sulfuric acid or formic acid. The reaction product obtained is the compound of the formula IA in which $R^4$ is H, which can, if desired, also be used directly as a stabilizer. The crude product can be worked up by customary methods (for example recrystallization or distillation).

The compounds of the formula III can also be prepared analogously to known processes, for example by reacting a compound of the formula IV

(IV)

with a compound of the formula V $$Y-R^3 \qquad (V)$$

in which X, R', $R^{2'}$ and $R^3$ are as defined above and Y is halogen, preferably Cl. The reaction temperature is preferably 20°-60° C.

If $R^{2'}$ in the compounds of the formula III is dimethylene or 1,2-propylene, these compounds can also be prepared by reacting

(VI)

with $$H-X-R^3 \qquad (VII)$$

in which X, R' and $R^3$ are as defined above and R" is hydrogen or methyl.

The compounds of the formula IA in which $R^4$ is $C_2$-$C_5$alkoxycarbonyl or $C_2$-$C_5$alkanoyl, can be prepared by the following scheme of reactions:

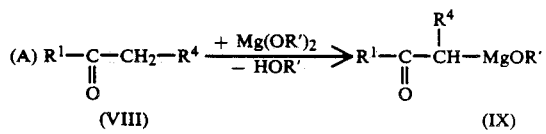

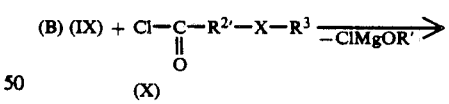

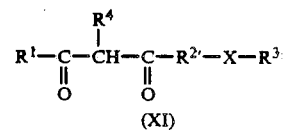

The variables $R^1$, $R^{2'}$, $R^3$, $R^4$, X and R' are as defined above.

The reactions A and B can be carried out successively in one reaction vessel without isolating the compound IX. It is advantageous for the reaction medium to be an inert solvent, for example toluene or an ether, in particular diethyl ether or tetrahydrofuran. The reaction A is preferably carried out at 5° to 15° C. and the reaction B at 0° to 25° C.

If $R^{2'}$ is trimethylene, the compounds of the formula X can be prepared, for example, by reacting a compound of the formula VII with γ-butyrolactone and subsequently converting the resulting carboxylic acid into the corresponding carboxylic acid chloride.

The compounds of the formula IA in which $R^4$ is hydrogen can also be prepared by decarboxylating the compound XIa.

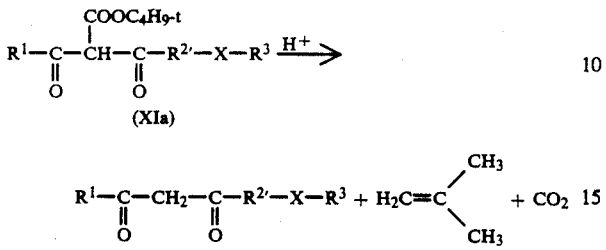
(XIa)

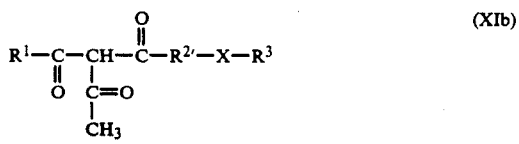

The decarboxylation is advantageously carried out under cationic conditions at approx. 60° to 80° C.

Investigations relevant to the method of synthesis described above originate from A. Treibs and K. Hintermeier; Chem. Ber., 1163-1166 (1954).

It is also possible to prepare compounds of the formula IA in which $R^4$ is hydrogen via the triacetylmethane derivative of the formula XIb

(XIb)

The compound of the formula XIb is converted into the corresponding compound of the formula IA by splitting off an acetyl radical.

The compounds of the formula XIb can also be prepared by reacting a compound of the formula VIIIa $$R^1-C(=O)-CH_2-C(=O)-CH_3$$ (VIIIa)

with an acid chloride of the formula X.

The ether-carboxylic or thioether-carboxylic acid chlorides of the formula X which are required for the synthesis of the compounds according to the invention can be prepared by conventional processes, for example by reacting the ether-carboxylic or thioether-carboxylic acids with thionyl chloride.

The compounds of the formula IA in which $R^{2'}$ is 1,2-propylene and $R^4$ is hydrogen can also be prepared, for example, in a manner known per se in accordance with the following equation:

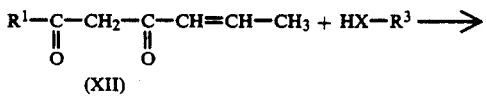
(XII)

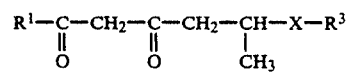

If they are not available commercially or have not previously been described, the starting materials used in the processes of preparation described above can be prepared by known processes.

The following examples illustrate the invention in greater detail. Unless otherwise stated, all quantity data are parts by weight.

EXAMPLE 1

Preparation of 1-benzylthio-4-tert-butoxycarbonyl-3,5-hexanedione

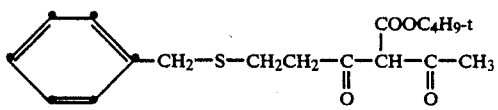

10.7 g (0.44 mol) of magnesium, 2 ml of chloroform and 46 g (1 mol) of absolute ethanol are initially placed, with the exclusion of moisture, in a 1 1 flask equipped with a stirrer, a thermometer, a dropping funnel and a reflux condenser, and are heated under reflux for 1 hour, with stirring. 300 ml of diethyl ether are then added dropwise and the mixture is stirred for 1.5 hours. The mixture is then cooled to approx. 12° C. 63.2 g (0.4 mol) of tert-butyl acetoacetate are added dropwise at this temperature. The reaction mixture is cooled further to approx. $-3°$ C., and 85.8 g (0.4 mol) of benzylthiomethylacetyl chloride in 100 ml of absolute diethyl ether are added dropwise at this temperature in the course of 45 minutes. The mixture is then stirred for a further hour at approx. $-3°$ C. and is then stirred for a further 2 hours without cooling, in the course of which it reaches room temperature. The reaction mixture is stirred into 400 g of ice-water and 48 g of concentrated $H_2SO_4$. The organic phase is separated off and is washed with 150 ml of water, 100 ml of bicarbonate and 150 ml of water again and is then dried and concentrated.

Yield: 128.6 g ($=95.5\%$ of theory)
Refractive index: $n_D^{2°} = 1.5284$

EXAMPLES 2-9

The preparation of the following compounds is carried out analogously to Example 1.

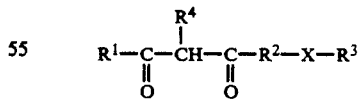

TABLE 1

| Example | $R^1$ | $R^2$ | $R^3$ | $R^4$ | X | refractive index |
|---|---|---|---|---|---|---|
| 2 | —$CH_3$ | —$CH_2CH_2$— | —$C_4H_9$-n | —$COOC_4H_9$-t | S | $n_D^{20} = 1.4813$ |
| 3 | —$CH_3$ | —$CH_2$— | —$C_4H_9$-t | —$COOC_4H_9$-t | S | $n_D^{20} = 1.4913$ |
| 4 | —$CH_3$ | —$CH_2$— | —$C_8H_{17}$-t | —$COOC_4H_9$-t | S | $n_D^{20} = 1.4930$ |

TABLE 1-continued

| Example | R¹ | R² | R³ | R⁴ | X | refractive index |
|---|---|---|---|---|---|---|
| 5 | —CH₃ | —CH₂CH₂— | —CH₂-phenyl | —COOC₂H₅ | S | $n_D^{20} = 1.5486$ |
| 6 | phenyl | —CH₂CH₂— | —C₄H₉-n | —COOC₂H₅ | S | $n_D^{20} = 1.5376$ |
| 7 | —CH₃ | —CH₂CH₂CH₂— | phenyl | —COOC₄H₉-t | S | $n_D^{20} = 1.5334$ |
| 8 | —CH₃ | —CH₂CH₂CH₂— | —C₁₂H₂₅-n | —COOC₄H₉-t | S | $n_D^{20} = 1.4768$ |
| 9 | —CH₃ | —CH₂CH₂CH₂— | phenyl | —COOC₄H₉-t | O | $n_D^{20} = 1.5106$ |

EXAMPLE 10

Preparation of 1-benzylthio-3,5-hexanedione

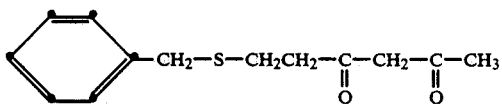

101 g (0.3 mol) of 1-benzylthio-4-tert-butoxycarbonyl-3,5-hexanedione (see Example 1) and 1.0 g of p-toluenesulfonic acid are heated at 70°-75° C. for 225 minutes in a 250 ml flask equipped with a stirrer, a thermometer, a reflux condenser and a bubble counter until the evolution of gas ($CO_2$) is complete. 100 ml of diethyl ether are added and the mixture is washed first with 50 ml of bicarbonate and then with 100 ml of water and is subsequently concentrated and fractionated.

Yield: 48.0 g (=67.7% of theory)
Boiling point: 122° C. at 0.001 bar

EXAMPLES 11-16

The preparation of the following compounds is effected analogously to Example 10, using the appropriate starting materials according to Table 1.

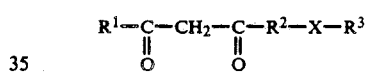

TABLE 2

| Example | R¹ | R² | R³ | X | refractive index melting point |
|---|---|---|---|---|---|
| 11 | —CH₃ | —CH₂CH₂— | —C₄H₉-n | S | $n_D^{20} = 1.4946$ |
| 12 | —CH₃ | —CH₂— | —C₄H₉-t | S | $n_D^{20} = 1.5005$ |
| 13 | —CH₃ | —CH₂— | —C₈H₁₇-t | S | $n_D^{20} = 1.5027$ |
| 14 | —CH₃ | —CH₂CH₂CH₂— | phenyl | S | m.p. = 29° C. |
| 15 | —CH₃ | —CH₂CH₂CH₂— | —C₁₂H₂₅-n | S | m.p. = 33° C. |
| 16 | —CH₃ | —CH₂CH₂CH₂— | phenyl | O | m.p. = 39° C. |

EXAMPLE 17

Preparation of 1-benzylthio-4-benzoyl-3,5-hexanedione

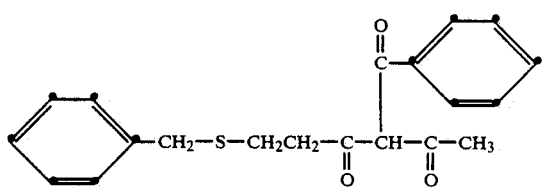

The preparation is carried out analogously to Example 1, employing 0.4 mol of benzoylacetone instead of 0.4 mol of tert-butyl acetoacetate.

Yield: 129.8 g (=95.3% of theory)
Refractive index: $n_D^{20} = 1.6000$

EXAMPLE 18

Preparation of 1-benzylthio-5-phenyl-3,5-pentanedione

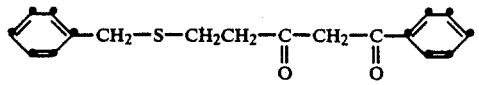

34.0 g (0.1 mol) of 1-benzylthio-4-benzoyl-3,5-hexanedione (see Example 17) are initially placed in a 100 ml flask equipped with a thermometer, a stirrer, a dropping funnel and a reflux condenser. 19.8 g (0.11 mol) of sodium methylate solution (30% in methanol) are added dropwise, with stirring, in the course of 40 minutes. In the course of this the reaction temperature rises from room temperature to approx. 32° C. The mixture is stirred for a further hour at room temperature and for a further 3 hours at approx. 45° C. and is then cooled to room temperature and stirred into 200 ml of water and 12 g of concentrated H₂SO₄. 180 ml of diethyl ether are added and the organic phase is separated off. The aqueous phase is washed with a further 50 ml of diethyl ether. The combined organic phases are washed with water, sodium bicarbonate and water again and are then dried, concentrated and fractionated. The resulting product, which has a boiling point of 180°-183° C. at 0.001 bar, is recrystallized from 20 ml of isopropanol.

Melting point: 55°-56° C.

EXAMPLE 19

Preparation of 1-n-hexylthio-5,5-dimethyl-2,4-hexanedione

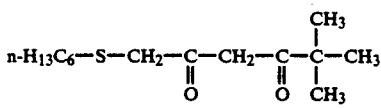

250 ml of toluene and 99 g (0.55 mol) of sodium methylate solution (30% in methanol) are initially placed in a flask equipped with a thermometer, a stirrer, a dropping funnel and a distillation bridge with receiver, and 108.4 g of a methanol/toluene mixture are distilled off until the reaction temperature reaches 109° C. 60 g (0.6 mol) of pinacolone are then added dropwise at the same temperature and 95 g (0.5 mol) of methyl n-hexylthioacetate are added dropwise in the course of 20 minutes. In the course of this a further 32.5 g of a methanol/toluene mixture are distilled off. The mixture is then stirred for a further 35 minutes at 106° C. and is worked up analogously to Example 18. The residue is concentrated and then fractionated in vacuo.

Boiling point: 130°-140° C. at 0.2 bar
Refractive index: $n_D^{20} = 1.4890$

EXAMPLE 20

Preparation of 1-n-hexylthio-4-phenyl-2,4-butanedione

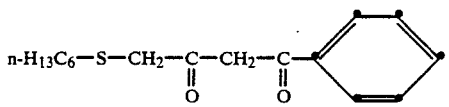

The compound is prepared analogously to Example 19.

Boiling point: 144°-148° C. at 0.1 bar
Refractive index: $n_D^{20} = 1.5786$

EXAMPLE 21

Preparation of 1-n-butoxy-7,7-dimethyl-4,6-octanedione

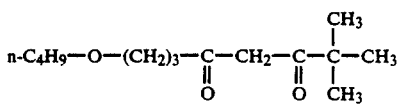

The compound is prepared analogously to Example 19.

Boiling point: 112°-116° C. at 1 bar
Refractive index: $n_D^{20} = 1.4532$

EXAMPLE 22

A dry mixture consisting of 100 parts of PVC (K value 64), 3 parts of epoxidized soya bean oil, 0.15 part of Zn stearate, 0.15 part of Ca stearate and 0.3 part of the stabilizer indicated in Table 3 is milled on mixing rolls for 5 minutes at 180° C. Samples of sheeting from the resulting rough sheet 0.3 mm thick are subjected to heat at 190° C. in a test oven (®Mathis Thermotester, type LTF-ST), and the Yellowness index (YI) as specified in ASTM D 1925 of a test sample is determined at the time intervals indicated. The results are shown in Table 3.

TABLE 3

| Stabilizer | YI after the following treatment time in minutes | | | | | | |
|---|---|---|---|---|---|---|---|
| | 3 | 5 | 7 | 9 | 11 | 13 | 15 |
| none | 42.3 | 47.1 | 48.4 | 52.4 | 67.4 | 83.8 | 95.1 |
| compound from Example 10 | 4.9 | 6.3 | 8.9 | 15.4 | 37.7 | 58.6 | 84.4 |

EXAMPLE 23

A dry mixture consisting of 100 parts of S-PVC (K value 70), 17 parts of dioctyl phthalate, 3 parts of epoxidized soya bean oil, 0.33 part of Zn oleate, 0.53 part of Ba p-t-butylbenzoate, 0.70 part of phenyldiisodecyl phosphite, 0.44 part of ®SHELL SOL A (mixture of aromatic hydrocarbons) and 0.2 part of the stabilizer indicated in Table 4 is milled on mixing rolls for 5 minutes at 180° C. Samples of sheeting from the resulting rough sheet 0.3 mm thick are subjected to heat at 180° C. in a test oven (®Mathis Thermotester, type LTF-St), and the Yellowness Index (YI) as specified in ASTM D 1925 of a test sample is determined at the time intervals indicated. The results are shown in Table 4.

TABLE 4

| Stabilizer | YI after the following treatment time in minutes | | | | | | |
|---|---|---|---|---|---|---|---|
| | 0 | 5 | 10 | 15 | 20 | 25 | 30 |
| none | 9.5 | 12.0 | 15.1 | 19.5 | 26.0 | 28.8 | 29.3 |
| Compound from Example 8 | 0.9 | 1.4 | 1.9 | 2.0 | 2.6 | 3.3 | 4.4 |
| Compound from Example 9 | 0.9 | 1.2 | 1.6 | 2.0 | 2.4 | 3.4 | 4.3 |
| Compound from Example 14 | 0.7 | 0.7 | 1.3 | 1.1 | 1.4 | 1.7 | 2.3 |
| Compound from Example 15 | 0.8 | 0.7 | 1.2 | 1.4 | 1.7 | 2.0 | 3.0 |
| Compound from Example 16 | 1.1 | 0.9 | 1.2 | 1.5 | 1.4 | 1.9 | 2.5 |

What is claimed is:

1. A compound of the formula I $$R^1-\underset{\underset{O}{\|}}{C}-\overset{\overset{R_4}{|}}{CH}-\underset{\underset{O}{\|}}{C}-R^2-X-R^3 \qquad (I)$$

in which $R^1$ and $R^3$ independently of one another are $C_1$–$C_{12}$alkyl, phenyl or phenyl which is substituted by one to three $C_1$–$C_{12}$alkyl groups, $R^2$ is $C_2$–$C_{10}$alkylene, $R^4$ is hydrogen, and X is oxygen or sulfur, subject to the proviso that the compound of the formula $$H_3C-\underset{\underset{O}{\|}}{C}-CH_2-\underset{\underset{O}{\|}}{C}-(CH_2)_7-S-\langle\text{phenyl}\rangle \quad \text{and is}$$

excluded.

2. A compound according to claim 1, in which X is sulfur.

3. A compound according to claim 1, in which $R^1$ is $C_1$–$C_6$alkyl, phenyl or phenyl which is substituted by one to three methyl groups and $R^3$ is $C_4$–$C_{12}$alkyl or phenyl.

4. A compound according to claim 1, in which $R^2$ is $C_2$–$C_4$alkylene.

5. A compound according to claim 1, in which $R^1$ is $C_1$–$C_4$alkyl or phenyl, $R^2$ is $C_2$–$C_4$alkylene and $R^3$ is $C_4$–$C_{12}$alkyl or phenyl.

6. The compound 1-phenylthio-4,6-heptanedione, 1-(n-dodecylthio)-4,6-heptanedione or 1-phenoxy-4,6-heptanedione according to claim 1.

7. A composition containing a chlorine-containing polymer selected from the group consisting of chlorinated homopolymers and copolymers of vinyl chloride, vinylidene chloride or chlorinated olefins, graft polymers of polyvinyl chloride with ethylene vinyl acetate, acrylonitrile-butadiene-styrene or methecrylonitrile-butadiene-styrene or mixtures thereof with polymers of acrylonitrile-butadiene styrene, methacrylonitrile-butadiene-styrene, styrene-butadiene, styrene-acrylonitrile or ethylene vinyl acetate and an effective stabilizing amount of a compound of the formula IA $$R^1-\underset{\underset{O}{\|}}{C}-\overset{\overset{R^4}{|}}{CH}-\underset{\underset{O}{\|}}{C}-R^{2'}-X-R^3 \qquad (IA)$$

in which $R^1$ and $R^3$ independently of one another are $C_1$–$C_{12}$alkyl, phenyl or phenyl which is substituted by one to three $C_1$–$C_{12}$alkyl groups, $R^{2'}$ is $C_1$–$C_{10}$alkylene, $R^4$ is hydrogen, and X is oxygen or sulfur.

8. A composition according to claim 7, in which X is sulfur.

9. A composition according to claim 7, in which $R^{2'}$ is $C_2$–$C_{10}$alkylene.

10. A composition according to claim 7, containing, in addition, an epoxy compound and at least one Me(II) carboxylate and/or Me(II) phenate in which Me(II) is Ba, Ca, Mg, Cd or Zn.

11. A composition according to claim 7, containing, in addition, epoxidized soya bean oil and at least one Me(II) carboxylate in which Me(II) is Ba, Ca, Mg or Zn.

12. A composition according to claim 10, containing, in addition, a phosphite.

13. A composition according to claim 7, wherein the chlorine-containing polymer is polyvinyl chloride.

14. A method for stabilizing a chlorine-containing polymer selected from the group consisting of chlorinated homopolymers and copolymers of vinyl chloride, vinylidene chloride or chlorinated olefins, graft polymers of polyvinyl chloride with ethylene vinyl acetate, acrylonitrile-butadiene-styrene or methacrylonitrile-butadiene-styrene or mixtures thereof with polymers of acrylonitrile-butadiene styrene, methacrylonitrile-butadiene-styrene, styrene-butadiene, styrene-acrylonitrile or ethylene vinyl acetate against the harmful effects of light and heat which comprises incorporating into the chlorine-containing polymer an effective stabilizing amount of a compound of the formula IA according to claim 7.

* * * * *